US006916289B2

(12) United States Patent
Schnall

(10) Patent No.: US 6,916,289 B2
(45) Date of Patent: Jul. 12, 2005

(54) PRESSURE APPLICATOR DEVICES PARTICULARLY USEFUL FOR NON-INVASIVE DETECTION OF MEDICAL CONDITIONS

(75) Inventor: Robert P. Schnall, Kiryat Bialik (IL)

(73) Assignee: Itamar Medical Ltd., Caesarea (IL)

( * ) Notice: Subject to any disclaimer, the term of this patent is extended or adjusted under 35 U.S.C. 154(b) by 0 days.

(21) Appl. No.: 10/851,137

(22) Filed: May 24, 2004

(65) Prior Publication Data

US 2004/0215085 A1 Oct. 28, 2004

Related U.S. Application Data

(62) Division of application No. 10/073,342, filed on Feb. 13, 2002, now abandoned, which is a division of application No. 09/485,302, filed as application No. PCT/IL99/00292 on Jun. 2, 1999, now Pat. No. 6,461,305.

(30) Foreign Application Priority Data

Jun. 7, 1998 (IL) ................................................ 124787

(51) Int. Cl.$^7$ ................................................ A61B 5/02
(52) U.S. Cl. ........................ 600/500; 600/485; 606/202; 602/13
(58) Field of Search ................................ 600/485–500, 600/335; 602/13; 606/201–204

(56) References Cited

U.S. PATENT DOCUMENTS

| 3,104,661 A | 9/1963 | Halpern ..................... 128/2.05 |
| 3,156,237 A | 11/1964 | Edmark, Jr. ................ 600/500 |
| 3,920,004 A | 11/1975 | Nakayama ................. 128/2.05 |
| 4,030,485 A | 6/1977 | Warner ...................... 128/2.05 |
| 4,112,491 A | 9/1978 | Bugay ........................ 364/415 |
| 4,280,506 A | 7/1981 | Zarcher ..................... 600/503 |
| 4,406,289 A | 9/1983 | Wesseling et al. ......... 128/670 |

(Continued)

FOREIGN PATENT DOCUMENTS

| EP | 0 465 345 | 1/1992 |
| WO | WO 98/04182 | 2/1998 |

OTHER PUBLICATIONS

Schnall, et al., "A rapid noninvasive blood pressure measurement method for discrete value and full waveform determination," *Journal of Applied Physiology*, pp. 307–314 (Jan. 1996).

Schnall, Abstract of Doctoral Thesis, "The Development of a New Blood Pressure Measurement Technique and its Application to the Study of Circulation," *Abstracts of Research Theses*, p. 68 (Sep. 1991).

Schnall, Research Thesis, "The Development of a New Blood Pressure Measurement Technique and its Application to the Study of the Circulation" (Sep. 14, 1990).

(Continued)

*Primary Examiner*—Robert L. Nasser
(74) *Attorney, Agent, or Firm*—Sughrue Mion, PLLC

(57) ABSTRACT

A probe for application to a body part particularly a finger of a patent to detect a change in the physical condition of the patient includes a housing defining a compartment closed at one end and open at the opposite end for receiving the distal end of the patient's finger and a medium wholly self-contained within the probe for applying a static pressure field substantially uniformly around the distal end of the patient's finger, of a predetermined magnitude sufficient to substantially prevent distention of the venous vasculature, uncontrolled venous backflow, and retrograde shockwave propagation into the distal end, and to partially unload the wall tension of, but not to occlude, the arteries in the distal end when at heart level or below. A sensor senses changes in the distal end of the patient's finger related to changes in arterial blood volume therein.

3 Claims, 14 Drawing Sheets

U.S. PATENT DOCUMENTS

| | | | |
|---|---|---|---|
| 4,437,470 A | | 3/1984 | Prost .......................... 128/679 |
| 4,667,672 A | * | 5/1987 | Romanowski .............. 606/202 |
| 4,677,984 A | | 7/1987 | Sramek ....................... 128/681 |
| 4,685,464 A | | 8/1987 | Goldberger et al. |
| 4,807,639 A | | 2/1989 | Shimizu et al. ............. 600/503 |
| 4,821,734 A | | 4/1989 | Koshino ..................... 128/680 |
| 4,836,219 A | | 6/1989 | Hobson et al. ............. 128/782 |
| 4,846,189 A | | 7/1989 | Sun ............................ 128/679 |
| 4,862,895 A | | 9/1989 | Yamasawa et al. ......... 128/680 |
| 4,926,867 A | | 5/1990 | Kanda et al. ............... 128/633 |
| 5,035,243 A | | 7/1991 | Muz ........................... 600/322 |
| 5,065,749 A | | 11/1991 | Hasebe et al. .............. 128/664 |
| 5,280,791 A | | 1/1994 | Lavie ......................... 128/696 |
| 5,301,675 A | | 4/1994 | Tomita ....................... 600/485 |
| 5,313,940 A | | 5/1994 | Fuse et al. |
| 5,337,744 A | | 8/1994 | Branigan .................... 128/633 |
| 5,339,810 A | | 8/1994 | Ivers et al. |
| 5,365,924 A | | 11/1994 | Erdman ...................... 128/633 |
| 5,438,986 A | | 8/1995 | Disch et al. ................ 128/633 |
| 5,542,421 A | | 8/1996 | Erdman ...................... 128/633 |
| 5,830,136 A | | 11/1998 | Delonzor et al. |
| 6,319,205 B1 | | 11/2001 | Goor et al. ................. 600/485 |
| 6,322,515 B1 | | 11/2001 | Goor et al. ................. 600/485 |
| 6,461,305 B1 | | 10/2002 | Schnall |
| 6,488,633 B1 | | 12/2002 | Schnall |

OTHER PUBLICATIONS

Guilleminault, et al., "A Cause of Excessive Daytime Sleepiness. The Upper Airway Resistance Syndrome," *Chest 104*, pp. 781–787 (1993).

Ludmer, et al., "Paradoxical Vasoconstriction Induced by Acetylcholine in Atherosclerotic Coronary Arteries," *New England Journal of Medicine*, vol. 315, No. 17, pp. 1046–1051 (1986).

Kuo, et al., "Endothelium–Dependent, Flow–Induced Dilation of Isolated Coronary Arterioles," *The American Physiological Society*, vol. 259, pp. H1063–H1070 (1990).

Dorlas, et al., "Photo–Electric Plethysmography as a Monitoring Device in Anaesthesia," *British Journal of Anaesthesia*, vol. 57, No. 5, pp. 524–530 (1985).

Nijboer, et al., "Comparison of Plethysmograms Taken From Finger and Pinna During Anaesthesia," *British Journal of Anaesthesia*, vol. 57, No. 5, pp. 531–534 (1985).

Jain, et al., "Prognostic Implications if Mental Stress–Induced Silent Left Ventricular Dysfunction in Patients with Stable Angina Pectoris," *American Journal of Cardiology*, vol. 76, pp. 31–35 (1995).

Kurata, et al., "Electrocardiographically and Symptomatically Silent Myocardial Ischemia During Excercise Testing," *Japanese Circulation Journal*, vol. 55, pp. 825–834 (1991).

Ishibashi, et al., "Evaluation of Symptomatic vs. Silent Myocardial Ischemia Using the Ambulatory Left Ventricular Function Monitor (VEST)," *Israel Journal of Medical Science*, vol. 25, No. 9, pp. 532–538 (1989).

Jiang, et al., "Mental Stress–Induced Myocardial Ischemia and Cardiac Events," *JAMA*, vol. 275, No. 21, pp. 1651–1656 (1996).

Rozanski, et al., "Impact of Psychological Factors of the Pathogenesis of Cardiovascular Disease and Implications for Therapy," *Circulation*, pp. 2192–2217 (1999).

Hedblad, et al., "Low pulse–wave amplitude during reactive leg hyperaemia: an independent, early marker for ischaemic heart disease and death. Results from the 21–year follow–up of the prospective cohort study 'Men born in 1914', Malmö, Sweden," *J. Int. Med.*, vol. 236, pp. 161–168 (1994).

Chapter 23, "Air plethysmography in arterial and venous disease," *Non–Invasive Diagnostic Techniques in Vascular Disease*, Third edition, E. F. Bernstein (ed.), Mosby, St. Louis (1985).

Chapter 59, "The pulse volume recorder in peripheral arterial disease," *Non–Invasive Diagnostic Techniques in Vascular Disease*, Third edition, E. F. Bernstein (ed.), Mosby, St. Louis (1985).

Edwards, et al., "The cutaneous vasoconstrictor response to venous stasis in normal in subjects with primary Raynaud's Disease," *Clin. Auton. Res.*, vol. 9, No. 5, pp. 225–262 (1999).

Ögren, et al., "Plethysmographic pulse wave amplitude and future leg arteriosclerosis," *Atherosclerosis*, vol. 113, pp. 55–62 (1995).

\* cited by examiner

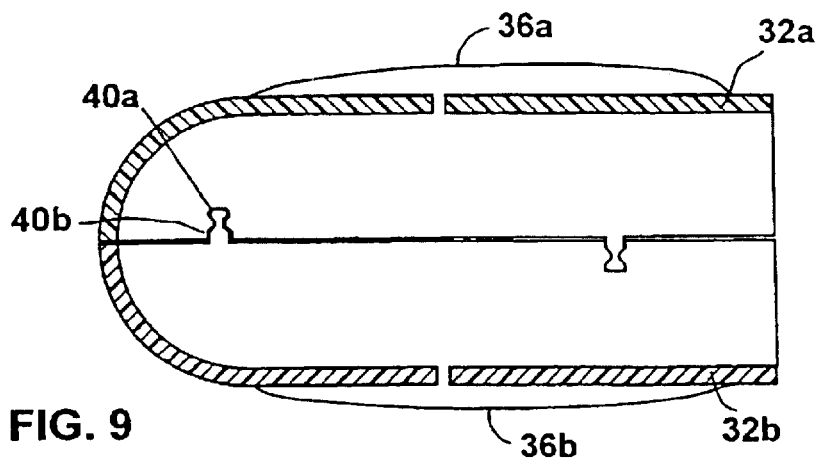
FIG. 9
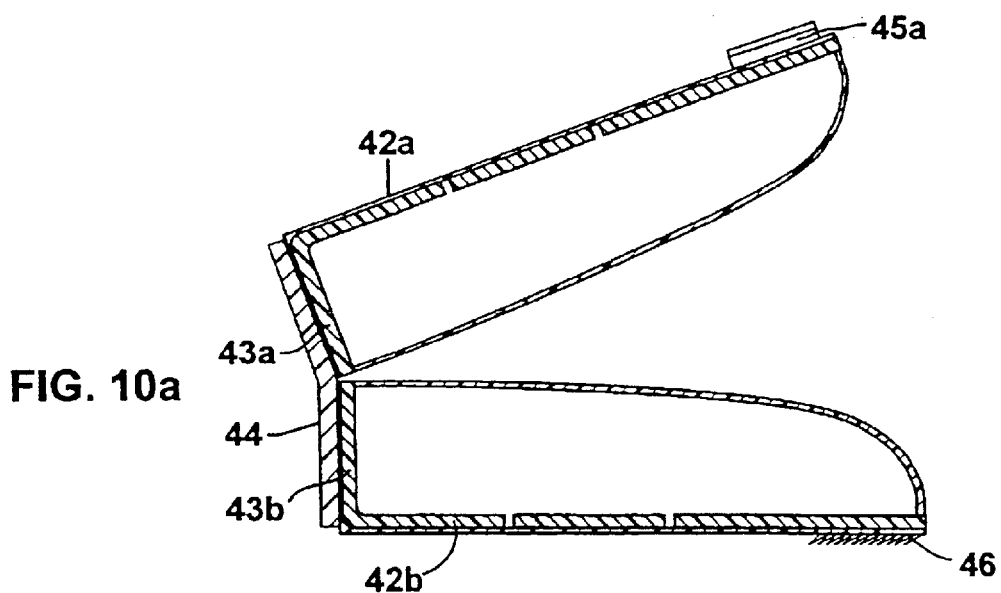
FIG. 10a
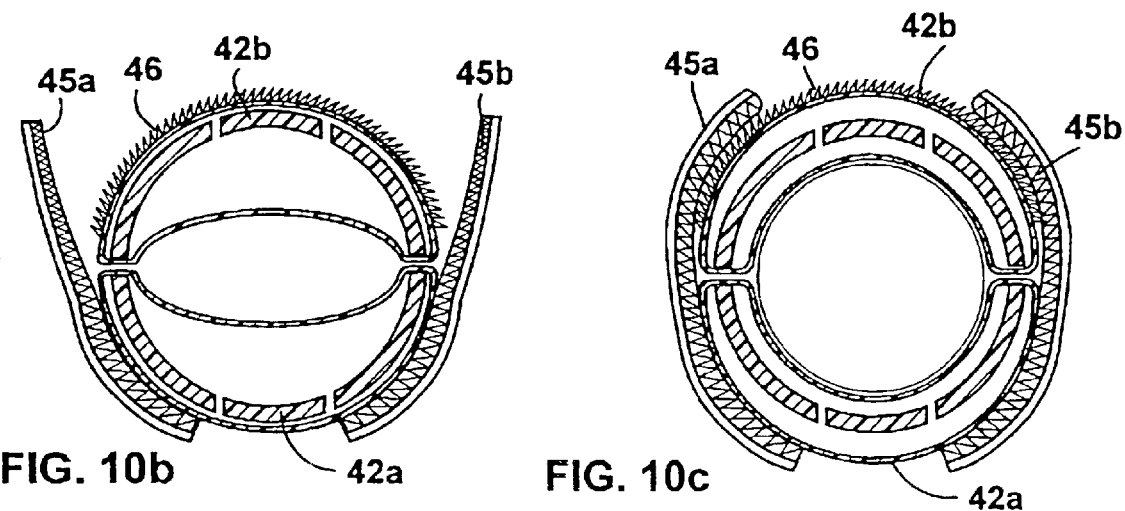
FIG. 10b  FIG. 10c

PRESSURE APPLICATOR DEVICES PARTICULARLY USEFUL FOR NON-INVASIVE DETECTION OF MEDICAL CONDITIONS

CROSS-REFERENCE TO RELATED APPLICATIONS

This application is a division of application Ser. No. 10/073,342 filed Feb. 13, 2002 abandoned, which is a division of application Ser. No. 09/485,302 filed Feb. 8, 2000 (now U.S. Pat. No. 6,461,305 issued Oct. 8, 2002), which is a National Stage Application filed under 35 U.S.C. §371 of International Patent Application No. PCT/IL99/00292 filed Jun. 2, 1999. The entire contents and disclosures of all of the preceding prior applications are incorporated herein by reference. The International Application of which priority benefit is claimed was published under PCT Article 21(2) in English.

FIELD AND BACKGROUND OF THE INVENTION

The present invention relates to pressure applicator devices for applying a predetermined static pressure to a body part of a patient. The invention is particularly useful as a probe for application to a digit (i.e., a finger or toe) of a patient for the non-invasive detection of certain medical conditions in accordance with the method described in our PCT Application PCT/IL97/00249; and the invention is therefore described below especially with respect to such applications.

Our Application PCT/IL97/00249 (WO98/04182, published Feb. 5, 1998) discloses methods and apparatus for the non-invasive detection of a change in a physiological condition of a patient by monitoring changes in the peripheral arterial tone as manifested by changes in the arterial blood volume in a terminal extremity of a body part, preferably a digit (finger or toe) of the patient. The method and apparatus are described in that application particularly for detecting mycardial ischemia and sleep apnea, and also for the continuous monitoring of blood pressure. The described apparatus includes a probe for application to the patient's body part (e.g., finger) which probe includes a housing for receiving the distal end of the patient's body part, and pressurizing means for applying a static pressure field substantially uniformly around the distal end of the patient's body part when received in the compartment, including its terminal-most extremity. The static pressure field is of a predetermined magnitude sufficient to substantially prevent distention of the venous vasculature, uncontrolled venous backflow, and retrograde shockwave propagation into the distal end of the body part, and to partially unload the wall tension of, but not to occlude, the arteries in the distal end of the body part when at heart level or below. The probe further includes a sensor within the housing for sensing changes in the distal end of the patient's body part related to changes in volume therein due to changes in instantaneous blood volume related to arterial tone.

That application described a number of probe constructions in which the static pressure field was applied via a remotely located pressure source connected by tubing to a fluid chamber within the probe. However, utilizing such remotely-located pressure sources complicates the construction of the apparatus and also restricts the mobility of the patient.

OBJECTS AND BRIEF SUMMARY OF THE PRESENT INVENTION

An object of the present invention is to provide a device particularly useful as a probe in the method and apparatus of the above-cited PCT Application but of a simplified or improved construction as compared to the devices described therein. Another object is to provide a probe which does not restrict the mobility of the patient.

According to broad aspect of the present invention, there is provided a device for application to a digit of a patient to detect a change in the physical condition of the patient; the device comprising a probe including: a housing defining a compartment closed at one end and open at the opposite end for receiving the distal end of the patient's body part; pressurizing means for applying a static pressure field substantially uniformly around the distal end of the patient's body part, when received in the compartment, including the extreme distal tip of the patient's body part, which static pressure field is of a predetermined magnitude sufficient to substantially prevent distention of the venous vasculature, uncontrolled venous backflow, and retrograde venous shockwave propagation into the distal end, and to partially unload the wall tension of, but not to occlude, the arteries in the distal end when at heart level or below; and a sensor for sensing changes in the distal end of the patient's body part related to changes in volume thereof due to changes in instantaneous blood volume related to arterial blood volume therein; characterized in that the pressurizing means for applying the static pressure substantially uniformly around the distal end of the patient's body part, including its terminal-most extremity, is constituted of a medium wholly self-contained within the probe.

A number of embodiments are described below for purposes of example.

According to further features in one class of embodiments described below, the pressurizing means includes an inner resilient within the housing and defining therewith an inner chamber to be filled with a fluid for applying the static pressure via the membrane substantially uniformly around the distal end of the patient's body part, including its terminal-most extremity.

According to further features in the latter described embodiments, the pressurizing means further includes an outer resilient membrane attached to the housing externally thereof and defining therewith an outer chamber communicating with the inner chamber via openings in the housing for enlarging the effective volume of the inner chamber such as to cause the inner membrane to apply substantially the same static pressure around the distal end of the patient's body part despite changes in volume therein.

A further embodiment is described below for purposes of example, wherein the pressure means includes a body of resilient sponge material formed with a recess defining the compartment for receiving the patient's body part when inserted therein.

The sensor within the housing is described below, for purposes of example, as being either an optical sensor for optically detecting, or a Hall Effect sensor for magnetically detecting, volume changes in the subject's finger which attend pulse-related blood volume changes and corresponding finger girth changes.

As will be described more particularly below, the present invention enables probes to be constructed with the static pressurizing means wholly self-contained within the probe housing, thereby greatly simplifying the construction of the probe as well as reducing restrictions on the mobility of the patient using such a probe. However, the invention may also be implemented in a two-section probe wherein one section includes a first housing attached to the body part and defining a part of the static pressurizing means, and the second section includes a second housing having another part of the static pressurizing means in fluid connection to the first section, the sensor being located within the second section.

While the invention is particularly useful in the methods and apparatus of the above-cited PCT Application, the invention, or various features thereof, can be used in other applications as will also be described below.

Further features and advantages of the invention will be apparent from the description below.

BRIEF DESCRIPTION OF THE DRAWINGS

The invention is herein described, by way of example only, with reference to the accompanying drawings, wherein:

FIG. 9 is a side elevational view diagrammatically illustrating a probe similar to that of FIGS. 8a–8c but including another fastening arrangement for fastening the two half-sections together;

FIGS. 10a–10c are views corresponding to FIGS. 8a–8c but illustrating another probe constructed in accordance with the present invention;

DESCRIPTION OF PREFERRED EMBODIMENTS

Figure 1:
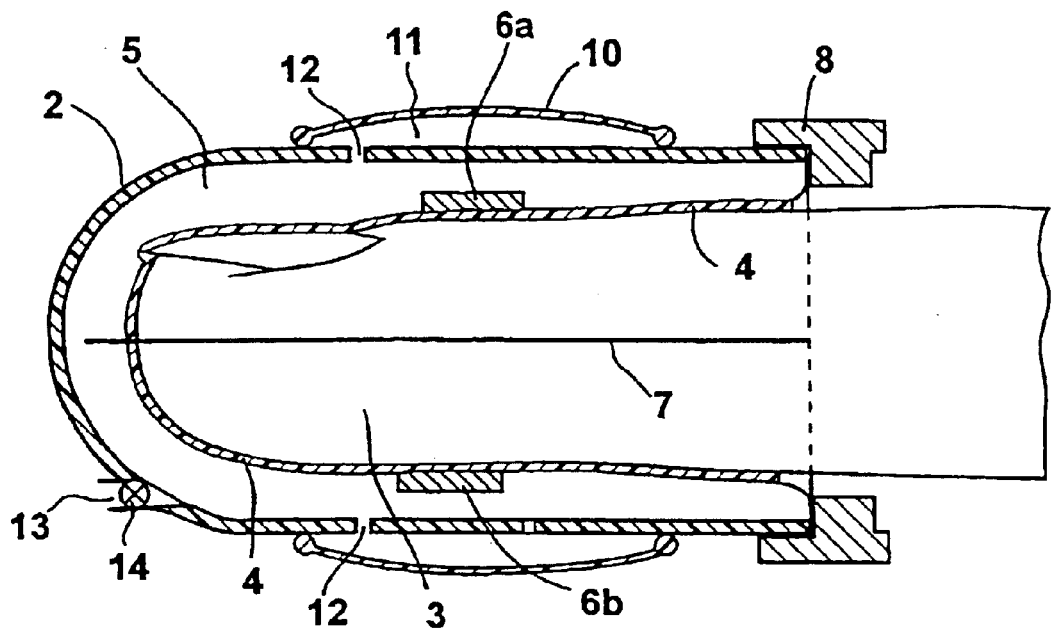
FIG. 1 is a longitudinal sectional view.
Figure 1A:
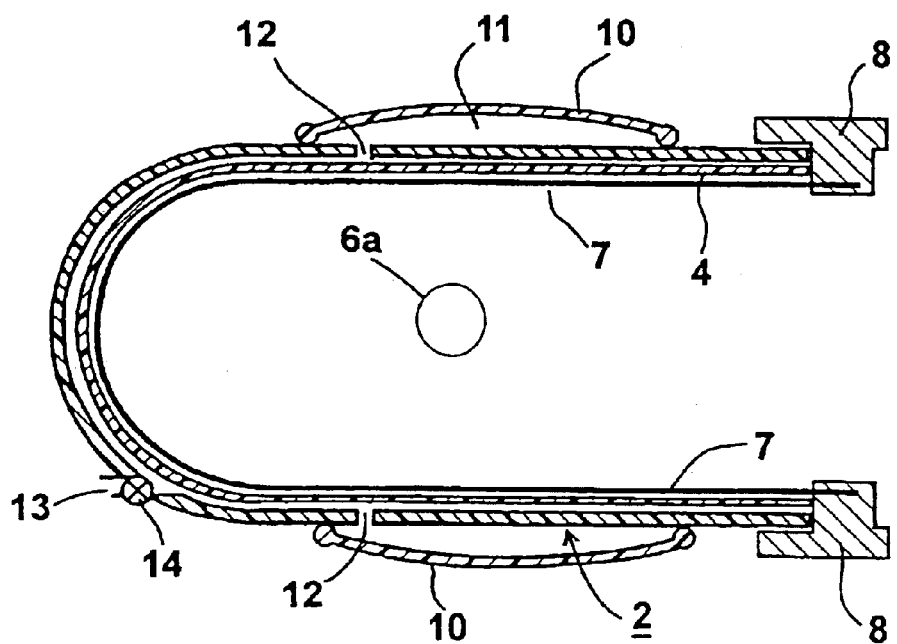
FIG. 1a is a corresponding view but rotated 90° with respect to FIG. 1, illustrating one form of finger probe constructed in accordance with the present invention.

FIGS. 1 and 1a illustrate one form of probe constructed in accordance with the present invention particularly for use in the method and apparatus of the above-cited PCT Application for monitoring the peripheral arterial tone of a patient's body part (e.g., digit) in order to indicate, in a non-invasive manner, the physiological state or medical condition of the patient. As briefly described above, and as more fully described in the above-cited PCT Application, such a probe includes pressurizing means for applying a static pressure field substantially uniformly around the distal end of the patient's digit, including its terminal-most extremity (extreme distal tip), and a sensor for sensing changes in the distal end of the patient's digit related to changes in volume thereof due to changes in instantaneous blood volume related to arterial blood volume therein. The probe illustrated in FIG. 1, however, is of a simplified construction as compared to the probes illustrated in the above-cited PCT Application, since the static pressure means in the probe of FIG. 1 is constituted of a medium wholly contained within the probe.

The probe illustrated in FIGS. 1 and 1a includes a housing 2 of rigid plastic material, closed at one end, and open at the opposite end, and defining a compartment for receiving the patient's finger 3. An inner membrane 4 within housing 2 defines therewith a chamber 5 for receiving a fluid, such as air, which applies a static pressure field substantially uniformly around the distal end of the finger 3 including its extreme distal tip. The probe illustrated in FIGS. 1 and 1a further includes a sensor constituted of one part 6a on one side of the finger, and another part 6b on the opposite side, for measuring changes in volume of the patient's finger caused by arterial blood flow. The illustrated probe further includes a U-shaped restraining bar 7 fixed by an annular ring 8 within the housing to cause the inner membrane 4 to more firmly grip the patient's finger 3 when inserted into the probe.

The above-cited PCT Application is hereby incorporated by reference for further details of the construction of the probe and the manner of its use for monitoring a physiological state or medical condition of the patient.

The probe illustrated in FIGS. 1 and 1a, however, differs from those described in the above-cited PCT Patent Application in the manner of providing the substantially uniform static pressure applied around the digital end of the patient's finger. Whereas in the examples illustrated in the above-cited PCT Application, such a static pressure is provided by a remotely-located pressure source coupled by tubing to the probe, the probe illustrated in FIGS. 1 and 1a includes a static pressurizing means which is wholly self-contained within the probe housing.

For this purpose, the probe illustrated in FIGS. 1 and 1a includes an outer resilient membrane 10 attached to the housing 2 externally thereof and defining with the housing an outer chamber 11. The outer membrane 10 is of annular configuration and is applied around an annular portion of the housing spaced from its tip such that the outer chamber 11 is of annular configuration. The outer annular chamber 11 communicates with the inner chamber 5 by means of a plurality of openings 12 formed through housing 2.

The outer membrane 10 enlarges the effective volume of the inner chamber 5 such as to cause, according to the Laplace Law, the inner membrane 4 to apply substantially the same static pressure around the distal end of the patient's finger 3 despite changes in volume in chamber 5. Thus, the Laplace Law broadly states that the distending pressure (P) within a distensible hollow object is equal at equalibrium to the tension in the wall (T) divided by the two principal radii of curvature of the object (R1, R2); that is $P=T(1/R1+1/R2)$. In a sphere, $R1=R2$; therefore $P=2T/R$. When the wall tension and the radius vary in direction proportion to each other (i.e., T/R is constant), as is substantially the case for rubber balloons for most of the range above the minimum distention and below the maximum distention, the balloon distending pressure remains substantially constant irrespective of changes in volume.

Figure 2:
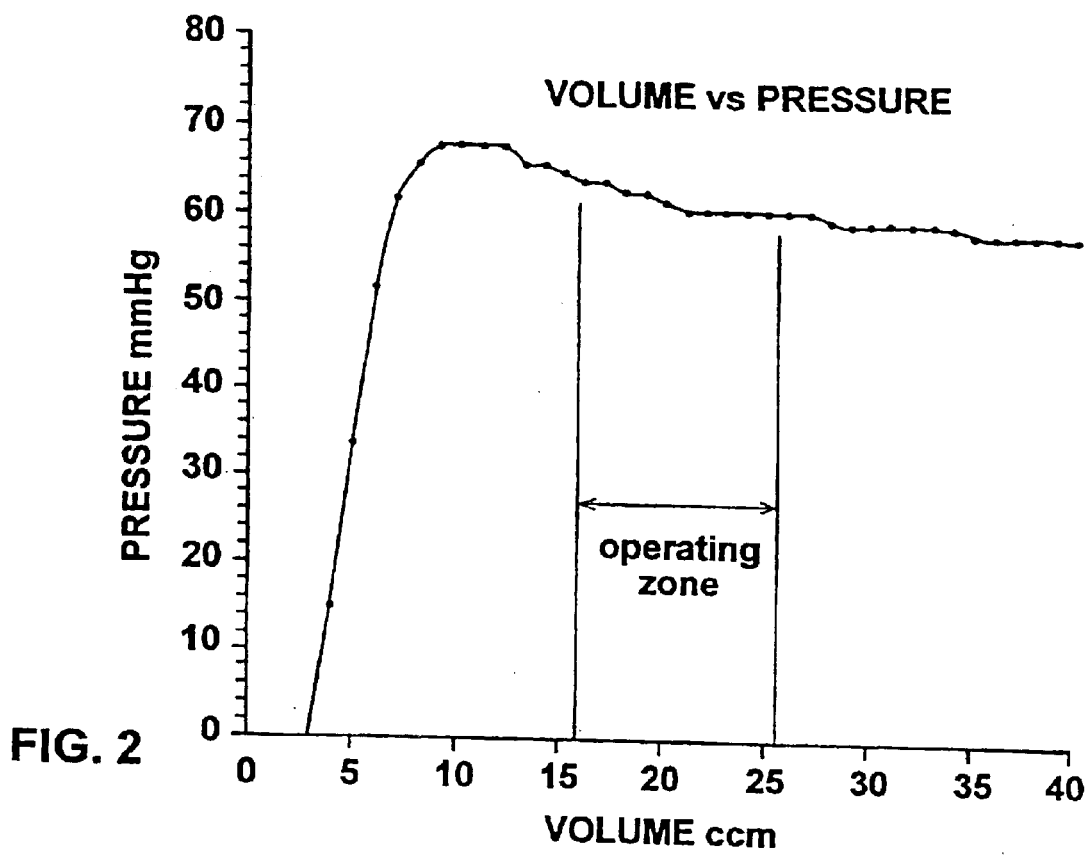
FIG. 2 is a graph of volume versus pressure.

FIG. 2 illustrates the relationship of pressure with respect to volume and particularly shows the relatively large operating zone in which the pressure remains substantially constant with the changes in volume. The actual pressure value is a function of the thickness and mechanical characteristics of the distensible material.

The probe illustrated in FIGS. 1 and 1a effectively enlarges the volume of the inner chamber 5 by the volume of the outer chamber 11 communicating with the inner chamber via openings 12 in the housing 2 such that the static pressure applied by the fluid within chamber 5 remains substantially constant irrespective of changes in volume of chamber 5 caused by arterial blood flow within the patient's finger 3 received within the probe. If the finger is partially removed from within the probe, the remaining portion will still be subject to the same external pressure because of the Laplace Effect.

The application of near diastolic counterpressures (40–70 mmHg), over the entire surface of the distal phalanges of the finger, was found not to adversely affect tissue perfusion despite the knowledge that localized pressure applied to tissues can cause collapse of microcirculation. This is due to the fact that while arterial pressure exceeds the counterpressure permitting inflow of arterial blood, for blood to return via the veins venous pressure must overcome the applied external pressure. The induced elevation of venous pressure causes the upstream microcirculation to be pressurized to a pressure level intermediate between the outgoing venous blood and the incoming arterial blood; hence the transmural pressure of the microcirculation within the applied pressure field is greater than zero and collapse of the microcirculation is prevented.

The maintenance of fingertip surface temperature within a narrow range around 36° C., and the lack of a tendency for surface temperature to fall after 2 hours of 70 mmHg pressure application, supports the above described model of the preservation of microcirculatory patency and consequently adequate tissue perfusion, as does the fact that overnight application of the pressurized probed on over 120 fingers in 60 subjects was well tolerated with no deleterious effects.

Figure 3:
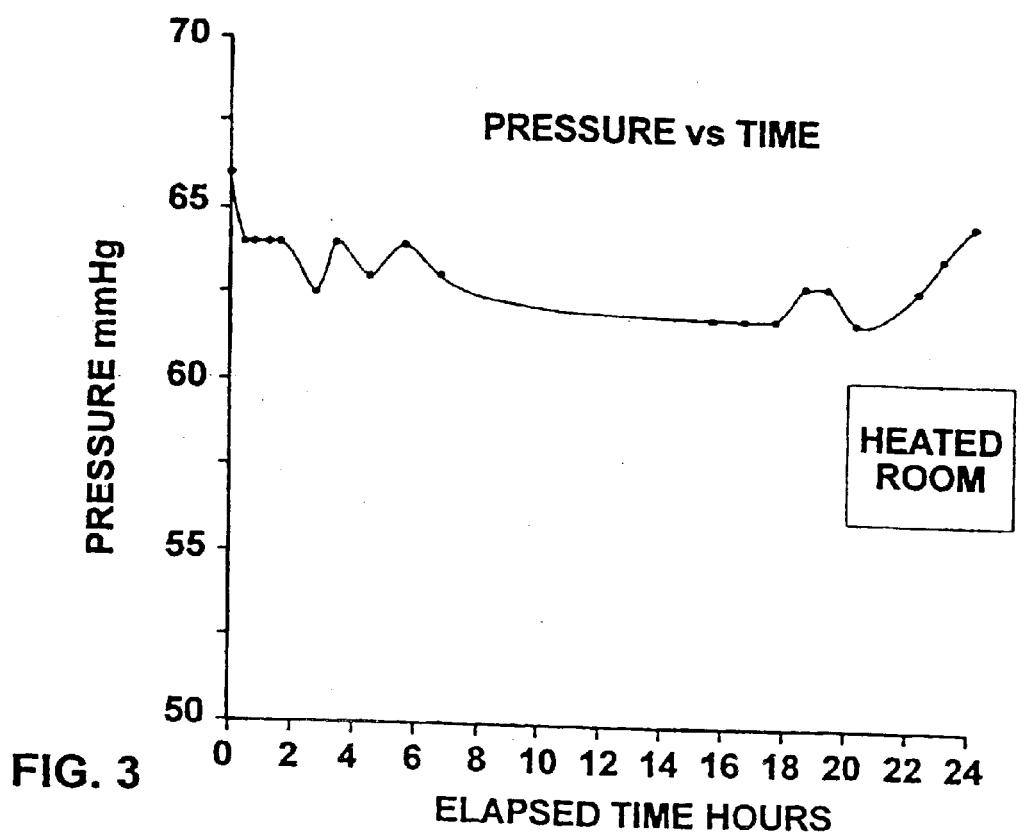
FIG. 3 is a graph of pressure versus time, both helpful in explaining the operation of the finger probe of FIG. 1.

In the probe illustrated in FIGS. 1 and 1a, the inner chamber 5 is initially filled with the fluid via a port 13 having a one-way valve 14 permitting the fluid (e.g., air) to flow into the chamber, but not out of the chamber. FIG. 3 illustrates how the pressure varies with time, and shows that after a fixed quantity of air has been added, the pressure within the device remains relatively constant over a 24-hour period.

Figure 4:
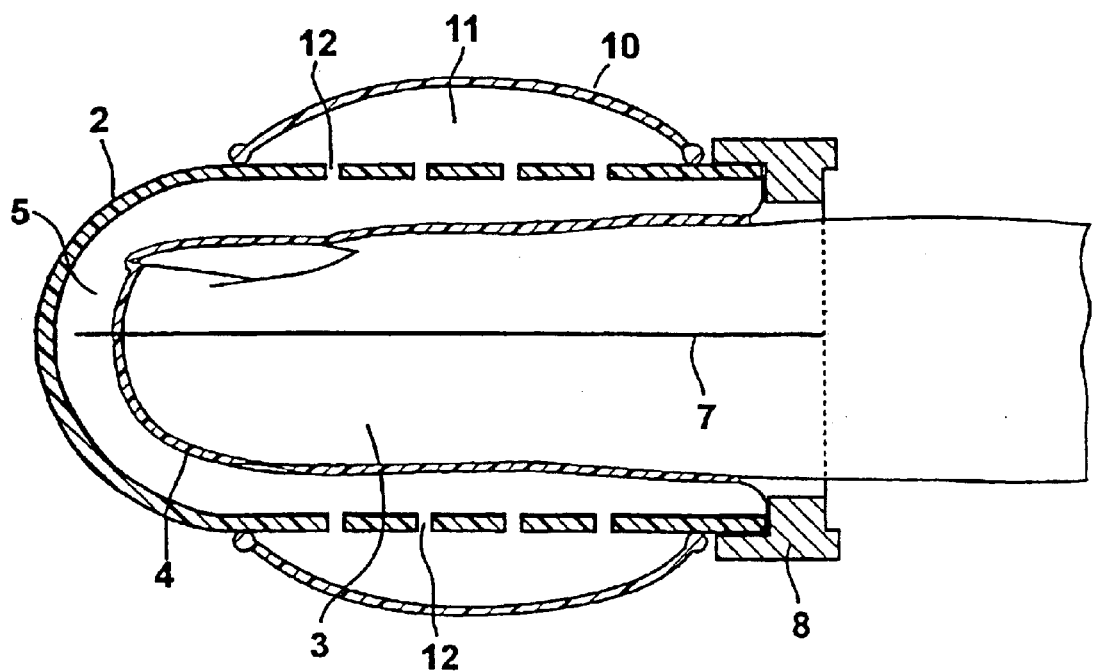
FIG. 4 is a view similar to that of FIG. 1, but omitting the sensor and illustrating a modification in the construction of the finger probe.

FIG. 4 illustrates a probe of the same construction as described above with respect to FIGS. 1 and 1a, except that the sensor elements have been omitted for simplification purposes. Also, the port 13 and the one-way valve 14 have been omitted, and instead a fixed volume of fluid is permanently confined within the space defined by the internal membrane 4 and the external membrane 10.

Figure 5:
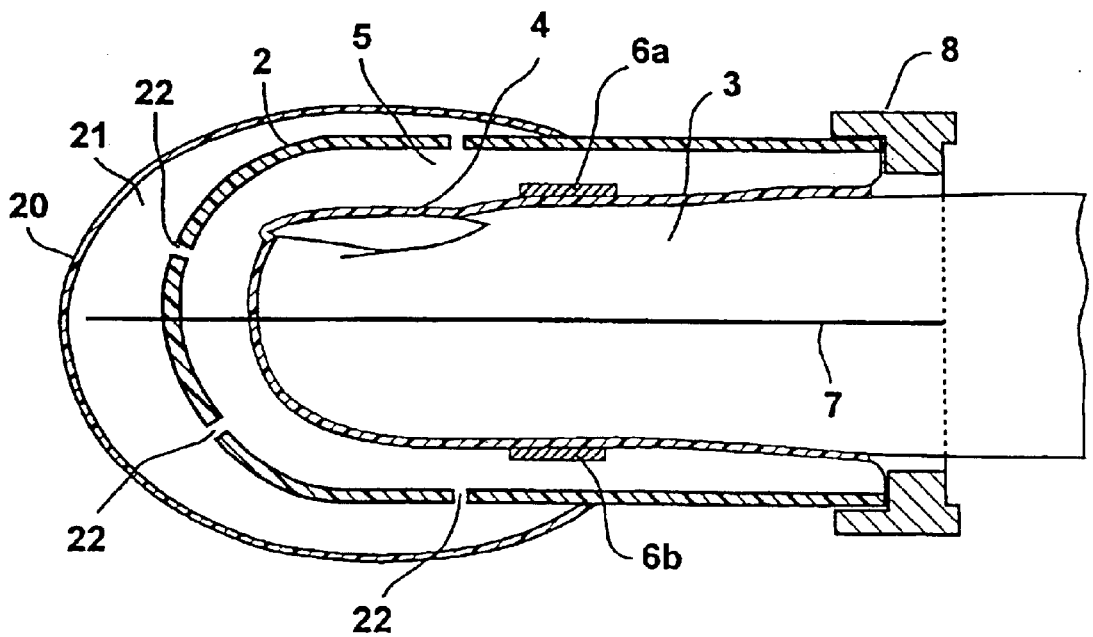
FIG. 5 is a view similar to that of FIG. 1, but illustrating another finger probe constructed in accordance with the present invention.

FIG. 5 illustrates a probe of similar construction as FIG. 4, except that the outer membrane 20 is of tubular configuration to define an outer chamber 21 with the distal tip of housing 2. The outer chamber 21 communicates with the inner chamber 5 via openings 22 formed in the housing tip, so as to effectively enlarge the volume of the inner chamber 5 to produce the relatively constant static pressure applied to the subject's finger 3 irrespective of changes in volume, as described above. Although FIG. 5 does not include the refill port or one-way valve, corresponding to elements 13 and 14 in FIGS. 1 and 1a, these elements could be included in which case they would be provided in the portion of housing 3 not covered by the outer membrane 21.

Figure 6A:
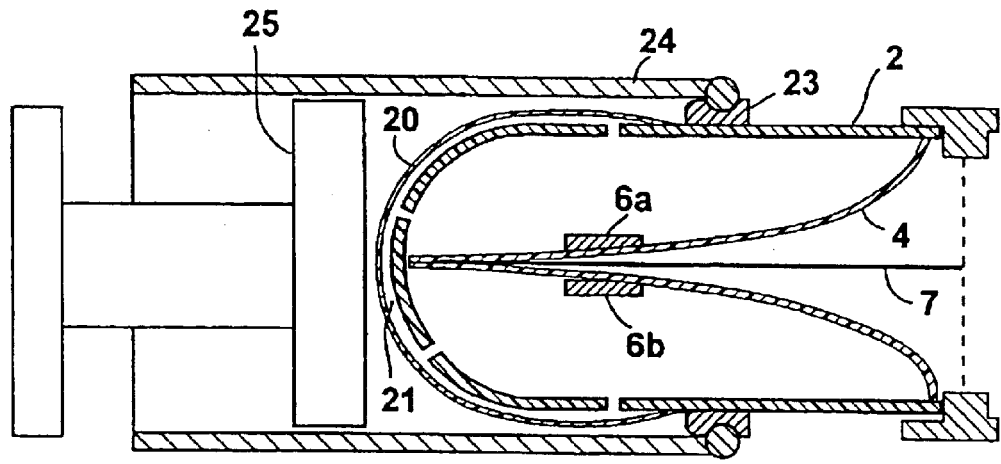
FIGS. 6a–6c diagrammatically illustrate one manner of applying the probe of FIG. 5 to a patient's finger.
Figure 6B:
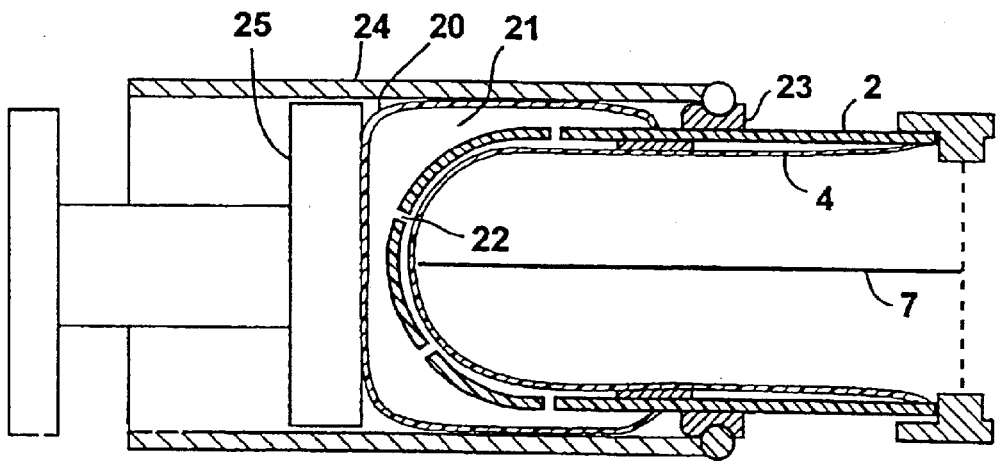
Figure 6C:
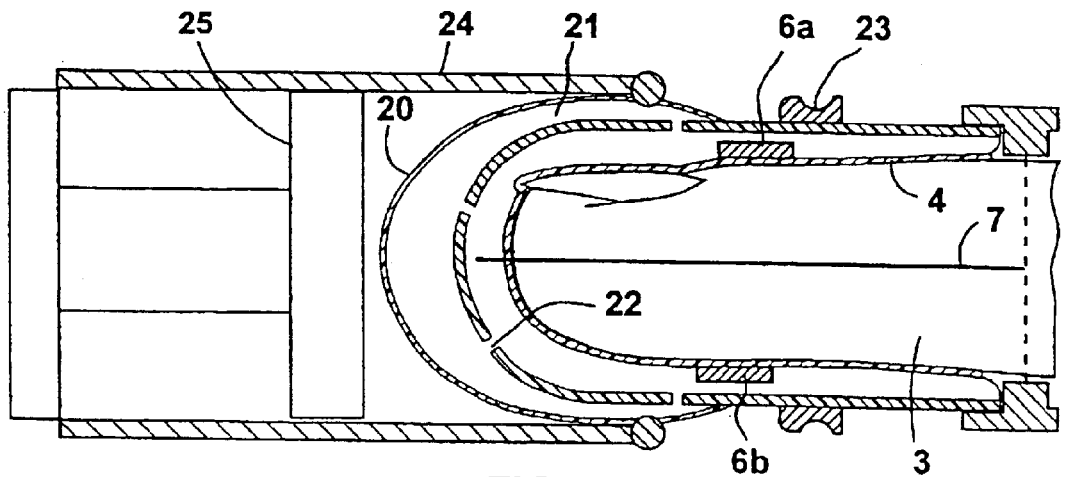

FIGS. 6a–6c illustrate one manner in which the probe constructed as in FIG. 5 may be manipulated to allow the patient's finger 3 to be inserted into the probe. For this purpose, housing 2 of the probe is provided with an annular ring 23 on the rigid portion of the housing spaced inwardly (proximally) from the outer membrane 20. A syringe including a cylinder 24 and a plunger 25 is used for shifting the fluid from the inner chamber 5 to the outer chamber 21 in order to permit the patient to insert the finger into the probe. FIG. 6a shows the open end of cylinder 24 applied to ring 23; FIG. 6b, shows the plunger 25 being retracted within its cylinder 24, to thereby draw the fluid within the inner chamber 5 into the outer chamber 21, permitting the subject to insert the finger into the probe, whereupon the plunger 25 may be returned to its normal position within its cylinder 24; and FIG. 6c shows the syringe being removed.

Figure 7A:
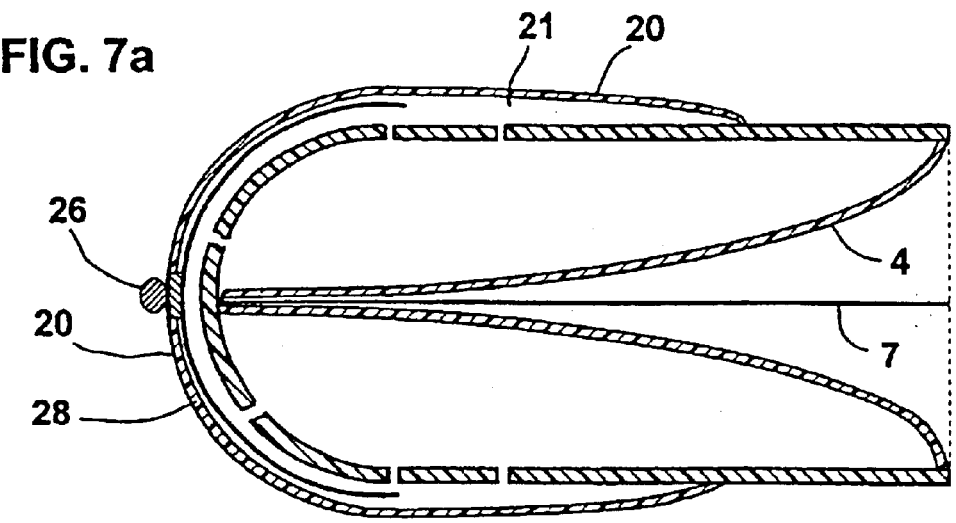
FIGS. 7a–7c illustrate a modification in the construction of the probe of FIG. 5, and the manner of applying it to the patient's finger.
Figure 7B:
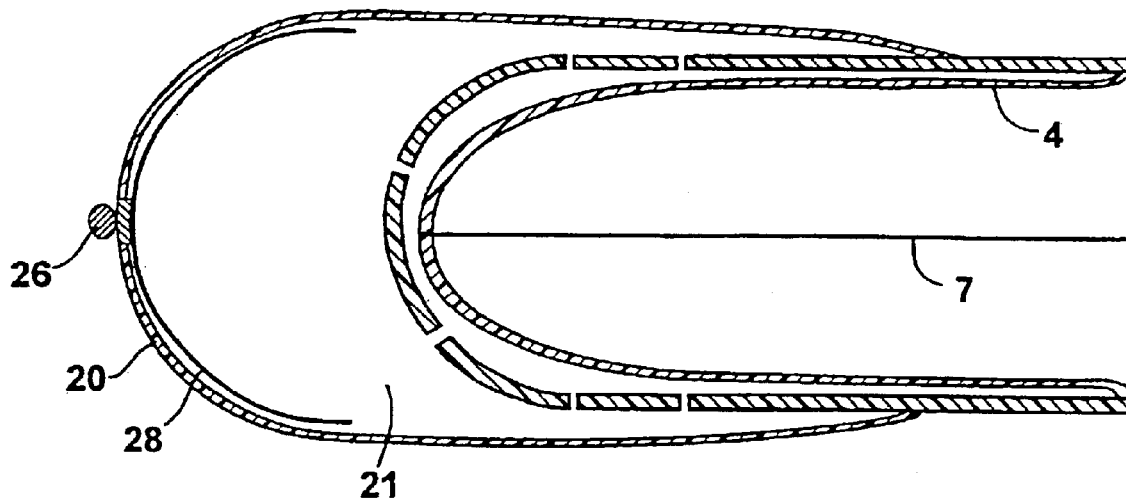
Figure 7C:
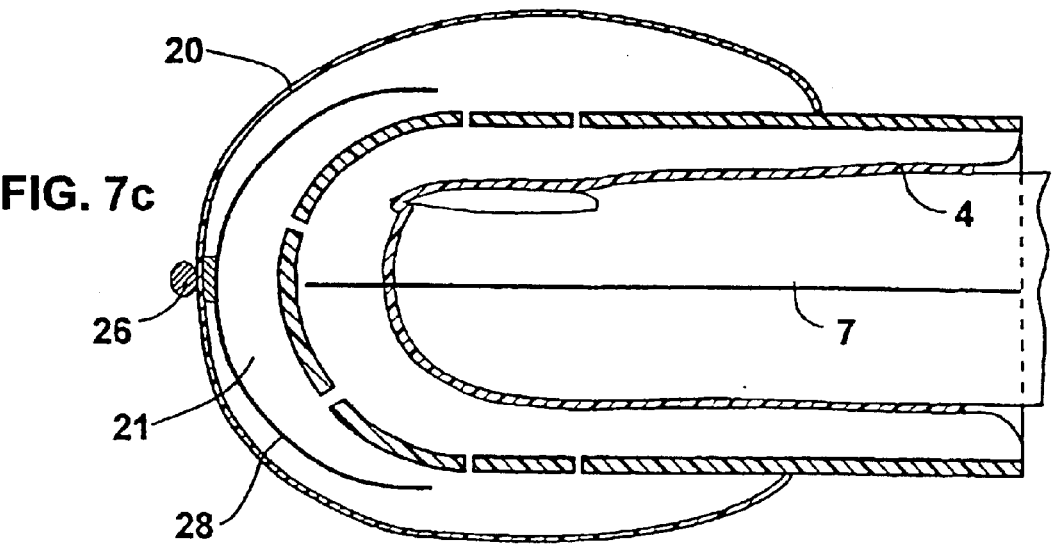

FIGS. 7a–7c illustrate another manner of manipulating the probe of FIG. 5 to permit insertion of the subject's finger. This is done by providing the outer membrane 20 with a finger piece including a knob 26 externally of the membrane and fixed to a backing member 28 engageing the inner surface of the membrane. Thus, knob 26 may be grasped by the user and pulled outwardly (FIG. 7b) to expand the outer chamber 21, thereby to draw into it the fluid from the inner chamber and to permit the patient to insert the finger 3 into the probe. After the patient's finger has thus been inserted, knob 26 may be released, whereupon the probe will assume the operative position illustrated in FIG. 7c.

The function of the outer membrane 20 in the construction of FIGS. 7a–7c is to facilitate the Laplace behavior as in the previously described designs.

Figure 8A:
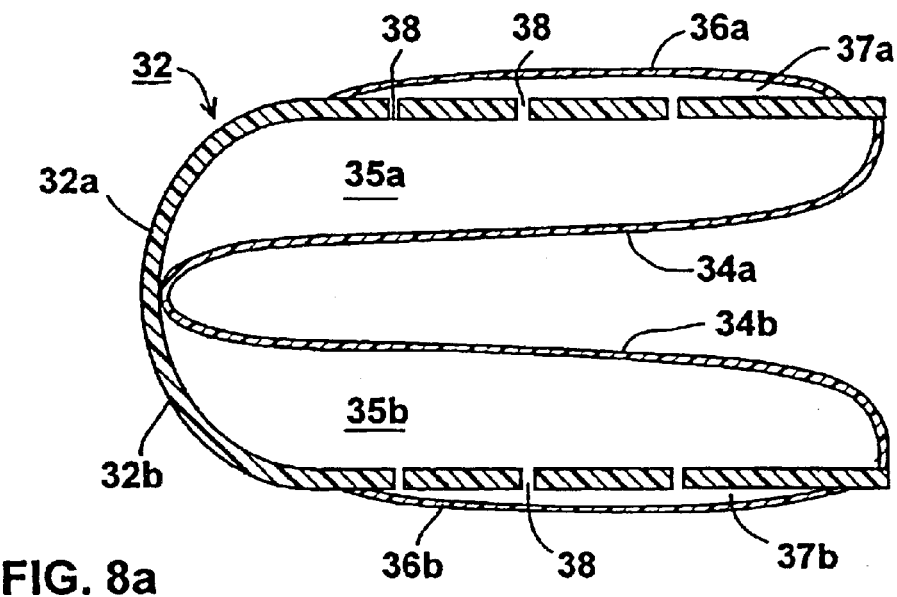
FIGS. 8a–8c diagrammatically illustrate another probe constructed in accordance with the present invention.
Figure 8B:
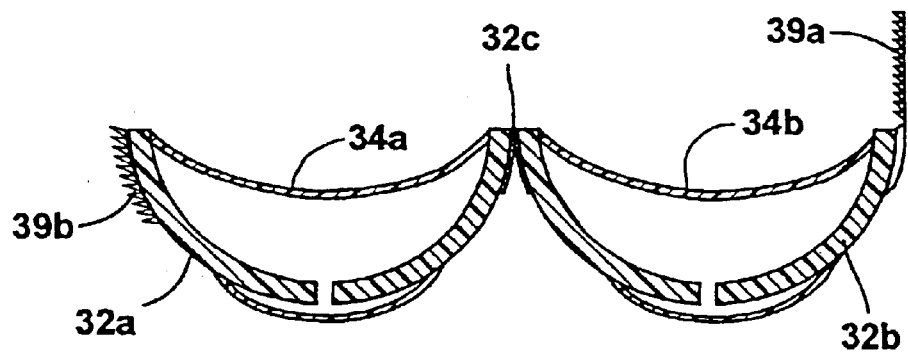
Figure 8C:
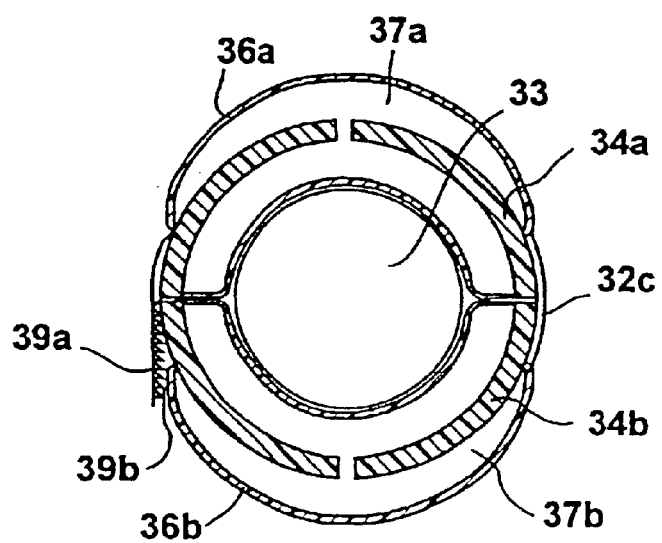

FIGS. 8a–8c diagrammatically illustrate a probe made of two sections hinged together to enable the probe to be opened (FIG. 8b) and closed around the patient's finger (FIG. 8c). Thus, as shown in FIG. 8a, the housing, generally designated 32, is also of tubular configuration closed at one end and open at the opposite end for the insertion of the finger 33. In this case, however, housing 32 is split into two half-sections 32a, 32b joined together along their length by an integral hinge 32c. Each housing section 32a, 32b includes an inner membrane strip 34a, 34b joined along the sides and end wall of the respective tubular section to define two internal chambers 35a, 35b. The probe further includes an outer membrane 36a, 36b for each housing section 32a, 32b attached to the outer surface of the respective housing section to define the two outer chambers 37a, 37b communicating with the two inner chambers 35a, 35b via openings 38 in the housing sections. The non-hinged sides of the two housing sections carry "Velcro" (T.M.) loop and hook fastener strips 39a, 39b, to enable the two sections to be tightly closed around the patient's finger 33 to apply the desired pressure thereto.

FIG. 9 illustrates a two-section construction similar to that of FIGS. 8a–8c, except that, instead of using "Velcro" (T.M.) fastener strips 39a, 39b to fasten the two sections together, the fastening elements in the construction illustrated in FIG. 9 include tongues 40a received within slots 40b integrally formed in the contacting edges of the two housing sections 32a, 32b.

FIGS. 10a–10c illustrate another two-section probe construction, but in this case the two half-sections 42a, 42b are hinged together at the adjacent edges of the two end walls 43a, 43b of each housing section. In addition, instead of using an integral hinge, the hinge is in the form of a flexible non-extensible strip 44 bonded to the two end walls 43a, 43b. The two half sections are secured in their closed conditions by two "Velcro" (T.M.) strips 45a, 45b fixed to one of the housing sections 42a at the open end of the housing and engageable with strips 46 fixed to the other housing section 42b. In all other respects, the construction of the probe illustrated in FIGS. 10a–10c is substantially the same as described above and includes the outer membrane defining the outer chamber communicating with the inner chamber to provide the above-described Laplace behavior.

Figure 11A:
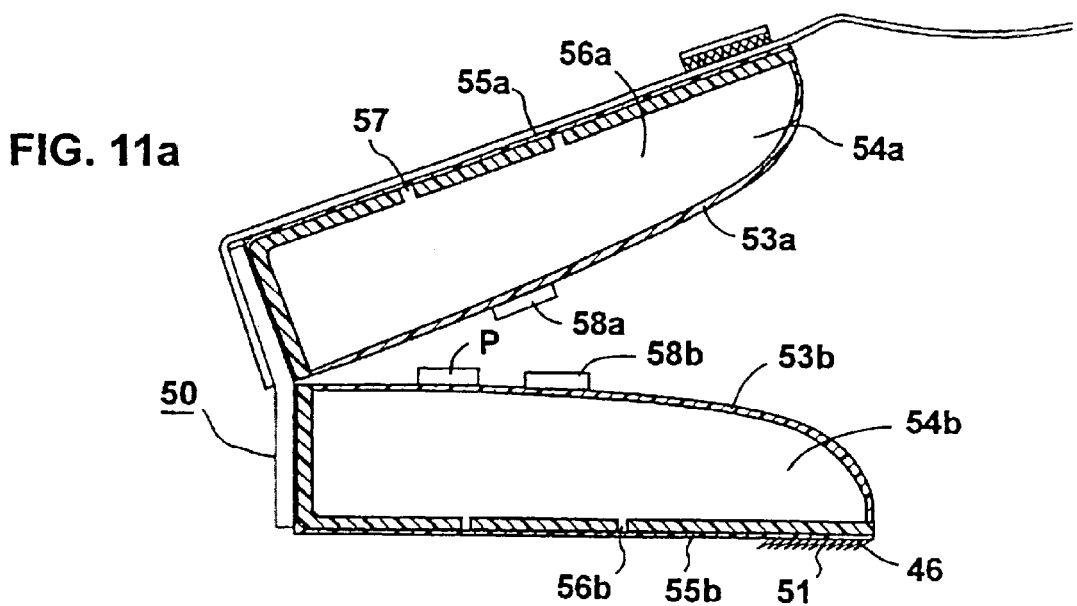
FIGS. 11a–11c illustrate another probe construction similar to that of FIGS. 10a–10c.
Figure 11B:
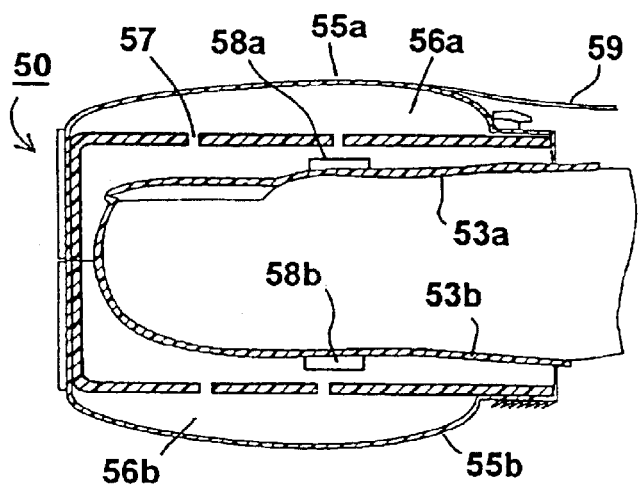
Figure 11C:
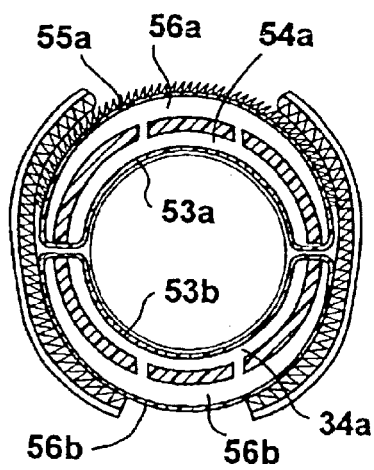
Figure 12:
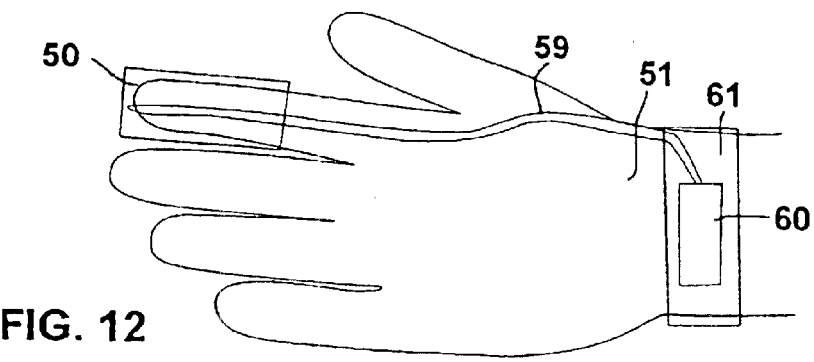
FIG. 12 illustrates one manner of applying to a patient the probe of FIGS. 11a–11c and a read-out to an electrical circuit.

FIGS. 11a–11c and 12 illustrate a probe 50 mounted on the finger of a hand 51 (FIG. 12). Probe 50 is of the two-section construction as in FIGS. 10a–10c, and as more particularly illustrated in FIGS. 11a–11c. The latter figures also illustrate the two-section inner membrane 53a, 53b defining the two-section inner chamber 54a, 54b, and the two-section outer membrane 55a, 55b defining the two-section outer chamber 56a, 56b communicating with the inner chambers via openings 57.

FIG. 11a further illustrates the two sensor elements 58a, 58b fixed to the two inner membranes 53a, 53b, so as to be located at the opposite sides of the finger when received within the compartment defined by the probe, as shown in FIG. 11b. The two sensor elements 58a, 58b are connected by electrical conductors 59 to an electrical circuit 60 (FIG. 12) fixed to a band 61, either directly connected, or by way of a glove. Electrical circuit 60, for example, could include the power supply and other circuitry for driving the sensor elements 58a, 58b, for receiving the outputs of those elements, and for storing the outputs, e.g., in a storage device, so as to eliminate the need for external electrical connections when the device is being used.

FIG. 11a further illustrates the provision of a pressure-sensitive switch P, or other pressure sensing device such as a strain gage, on inner membrane 53b, to ensure that leakage has not occurred, and that the appropriate pressure has been reached, when the probe is applied to the subject's finger. The pressure sensing device could be connected in series with the optical sensor, or in parallel to the control device.

While many of the drawings, such as FIGS. 4, 7a–7c, 8a–8c, 9 and 10a–10c, do not include the sensor elements corresponding to sensor elements 6a, 6b of FIGS. 1 and 1a and sensor elements 58a, 58b of FIGS. 11a–11c, it will be appreciated that these are omitted merely for purposes of simplifying the illustration and the description of these probes, and that such probes, when used for the particular applications described above, would also include such sensor elements. As indicated earlier, the sensor elements in all the described examples could be optical sensors, e.g., a light source (LED) and a light receiver for optically sensing the changes in the finger received within the probe; magnetic sensors, e.g., a permanent magnet and a magnetic field detector for sensing the changes in the finger girth by the Hall Effect; or other types of sensors, such as described in the above-cited PCT Patent Application.

Figure 13A:
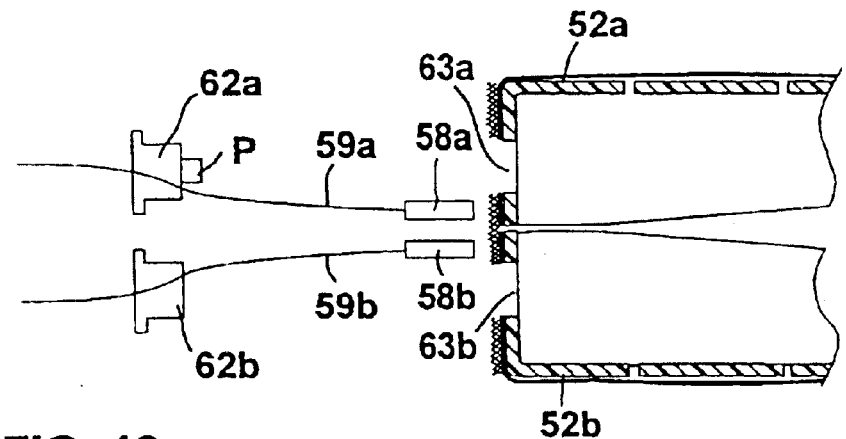
FIGS. 13a–13c diagrammatically illustrate another probe construction in accordance with the invention and showing particularly the elements of the sensor and the manner of making electrical connections to them.
Figure 13B:
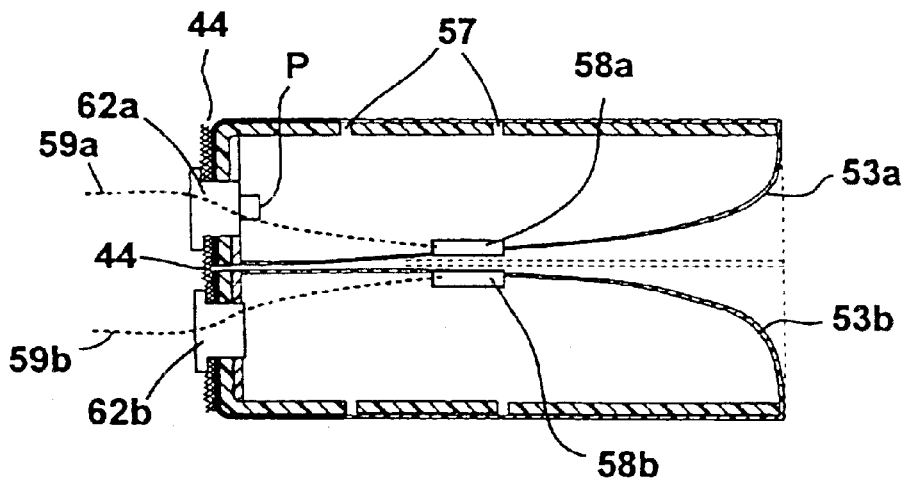
Figure 13C:
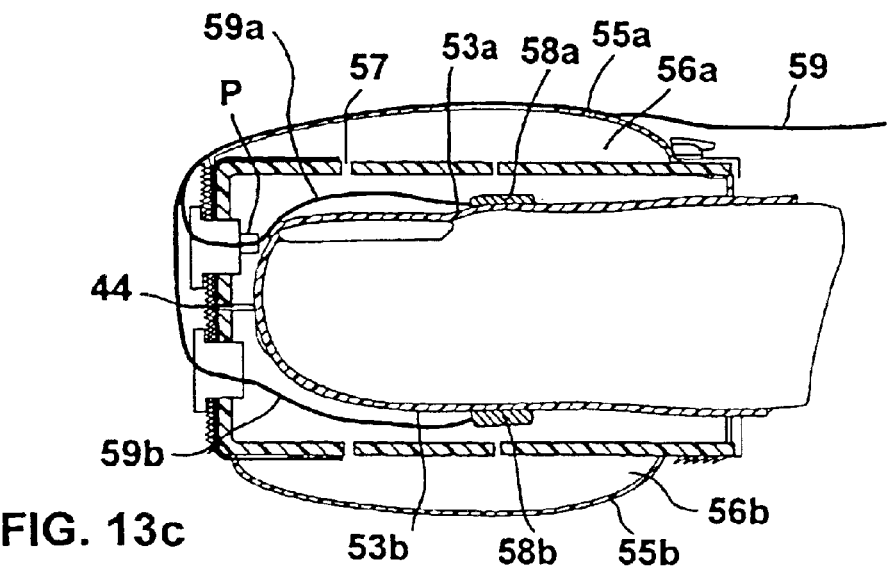

FIGS. 13a–13c illustrate one manner of mounting the sensor elements 58a, 58b in the finger probe, and making the external electrical connections to the sensor elements. Thus, each sensor element 58a, 58b is connected at one end to an electrical conductor 59a, 59b, having a rubber plug 62a, 62b, at the opposite end, to provide airtight seals in order to preserve the above described Laplace behavior. Plugs 62a, 62b are receivable within openings 63a, 63b in the walls of the two housing sections 52a, 52b hinged together by the strip 44 of flexible non-stretchable material. The two sensor elements 58a, 58b are fixed to the two diaphragms 53a, 53b within the compartment defined by the two housing sections 52a, 52b, such that when the sensor elements are assembled, and the two housing sections are in their closed condition as illustrated in FIG. 13c, the two sensor elements engage the opposite sides of the finger received within the housing compartment. The sensor elements output signals, via the electrical conductors 59a, 59b which pass through the housing wall, to the electrical processing and/or storage system, such as the electrical circuit 60 (FIG. 12) on the band 61 of the patient.

One of the plugs, e.g., plug 62a, could be provided with the pressure sensing device P to ensure leakage does not occur, and that the appropriate level of pressure has been reached, when the probe is applied, as described above with respect to FIG. 11a.

Figure 14:
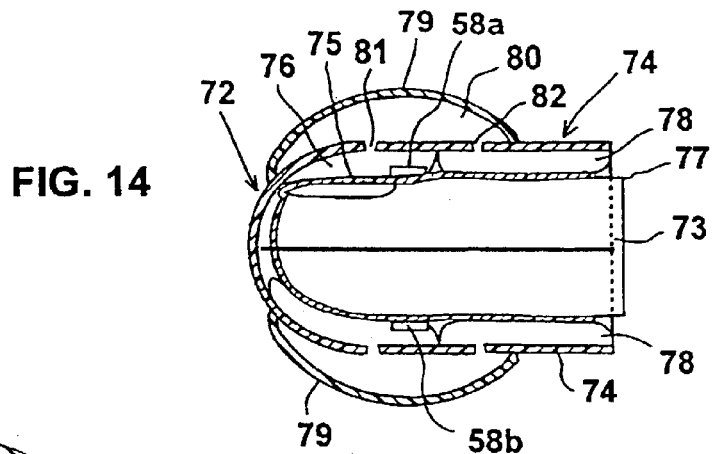
FIG. 14 illustrates a probe similar to that of FIG. 1 or 4 but including a pressure cuff contiguous to the inner (proximal) end of the probe for extending the pressure field with respect to the sensor elements.

FIG. 14 illustrates a finger probe having a thimble section 72 for receiving the end of the patient's finger 73 and an annular pressure cuff 74 contiguous to the open end of the thimble section 72 on the side nearer the heart of the patient when the probe is applied to the patient's finger. Such a pressure cuff extends the static pressure field past the sensor elements 58a, 58b towards the heart side of the patient as described in the above-cited PCT Application. In this case, an inner diaphragm 75 is attached around its periphery to the inner surface of the thimble section 72 to define therewith an inner chamber 76; and similarly, another inner diaphragm 77 is attached around its periphery to the inner surface of the annular cuff section 74 to define therewith an inner annular chamber 78. In addition, an outer diaphragm 79 is attached along one side of its periphery to the outer surface of the thimble section 72 and along the other side of its periphery to the outer surface of the annular section 74, to define with both sections a common outer chamber 80. The outer chamber 80 communicates with inner chamber 76 via openings 81 in the thimble section 72, and with inner chamber 78 via openings 82 in the annular cuff section 74.

The sensor elements 58a, 58b are located within the thimble section 72. This section applies the static pressure field described earlier substantially uniformly around the distal end of the subject's finger 73. This static pressure field is extended past the sensor elements towards the heart side of the patient by the inner chamber 78 defined by membrane 77 of the annular cuff section 74 as described in the above-cited PCT Application. In this case, however, the common outer chamber 80 defined by the outer membrane 79 maintains substantially the same static pressure field in both the thimble section 72 and the annular section 74 despite changes in volumes therein, according to the Laplace Law as described above.

In the above-described probes, the sensor elements (e.g., 6a, 6b in FIGS. 1a, 1b) are contained within the finger probe so as to be located on opposite sides of the patient's finger when inserted into the probe. In such arrangements, the sensor elements generate electrical signals which are outputted via electrical conductors to processing and/or storage circuitry, e.g., electrical conductor 59 and storage circuitry 60 in FIG. 12.

Figure 15:
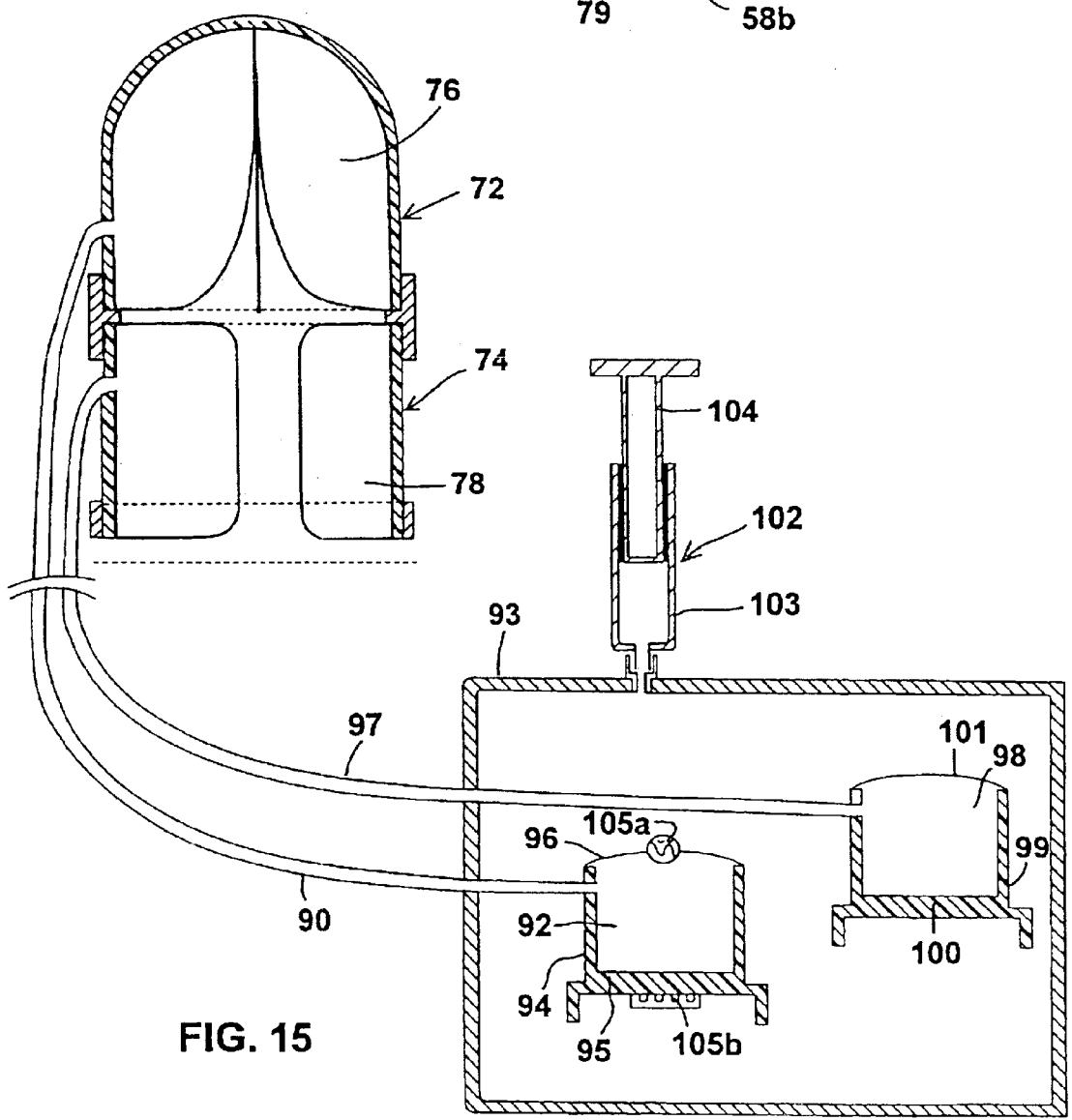
FIG. 15 illustrates another construction of a probe in accordance with another aspect of the invention.
Figure 16:
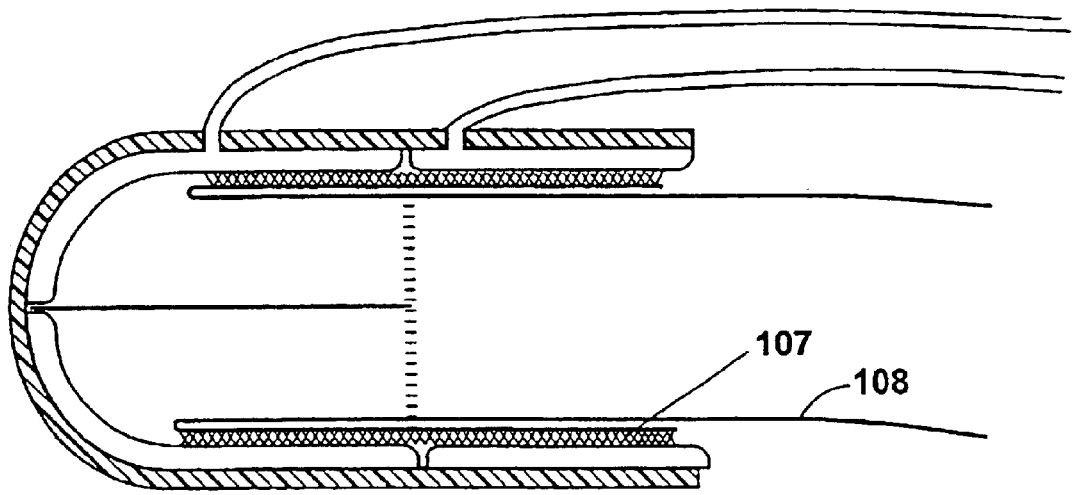
FIGS. 16 and 16a diagrammatically illustrate another probe construction in accordance with the present invention.

FIGS. 15 and 16 illustrate two arrangements wherein the sensor elements are not located in the housing of the finger probe, but rather in another housing separate from the finger probe and connected thereto by fluid tubes.

The probe illustrated in FIG. 15 is of the type illustrated in FIG. 14, including a thimble section 72 and an annular cuff section 74. The inner chamber 76 of the thimble section 72 is connected by a fluid tube 90 to a chamber 92 disposed within a second, rigid housing 93, which is preferably mounted close to the finger probe, e.g., on the subjects wrist. Chamber 92 is defined by a cylinder 94 closed at one end by an end wall 95, and at the opposite end by a membrane 96.

Annular chamber 78 of the cuff section 74 is connected via another tube 97 to another chamber 98 within the second housing 93. Chamber 98 is defined by a cylinder 99 closed at one end 100 and at the opposite end by another membrane 101.

It will be seen that the two chambers 92 and 98 within the second housing 93 will be subject to the same pressures as chamber 76 in the probe thimble section 72 and chamber 78 in the cuff section 74, respectively. These pressures will be opposed by the pressure within the second housing 93. The latter pressure may be preset by a syringe 102 including a cylinder 103 coupled to the interior of housing 93, and a plunger 104 which is movable in order to change the volume, and thereby the pressure, within housing 93.

Chamber 92, connected via tube 90 to the thimble section 72 of the probe, includes the sensor for sensing the volume changes within chamber 76 of the thimble section 72, and thereby the physical condition of the patient wearing the thimble. Thus, one sensor element 105a is fixed to membrane 96 so as to be displaced with that membrane, whereas the other sensor element 105b is fixed to the bottom wall 95 of the chamber 92, such that sensor elements 105a and 105b together can be used to measure the volume changes within chamber 94.

Although, the FIG. 15 arrangement does not provide the advantage of the previously-described arrangements in having the pressurizing means, for applying the static pressure substantially uniformly around the distal end of the patient's digit, to be constituted of a medium wholly self-contained within the finger probe, it does provide a number of other advantages: Thus, the thimble section 72 of the probe in FIG. 15 does not require an external chamber, as for example described with respect to FIGS. 1 and 1a, since chamber 94 within the second housing 93, if vented to the atmosphere, would act as the external chamber to provide the probe with the above-described Laplacian P/V characteristics. Also, if the housing is not vented to the atmosphere, this arrangement enables convenient presetting of the pressures in both the thimble section 72 of the probe, as well as in the annular cuff section 74.

This arrangement also simplifies the construction of the probe attached to the patient's finger since it locates the sensor elements in the separate housing 93 rather than in the probe itself. Thus, the thimble section of the probe could include two pliable plastic tubular elements each closed at one end and open at the opposite end, and located in the thimble section so as to engage the opposite sides of the patient's finger when inserted therein, such that each such element defines one-half of the pressurizing-chamber. Also, the cuff section 74 could be omitted.

Another possible advantage in the FIG. 15 arrangement is that it tends to avoid local bias towards smaller superficial blood vessels. Also housing 93 containing the sensor elements 105a, 105b, can be located very close to the finger-applied probe, such as on a wrist band (FIG. 12) to minimize the restrictions in the mobility of the patient and also the length of the fluid tubes 90, 97.

Figure 15A:
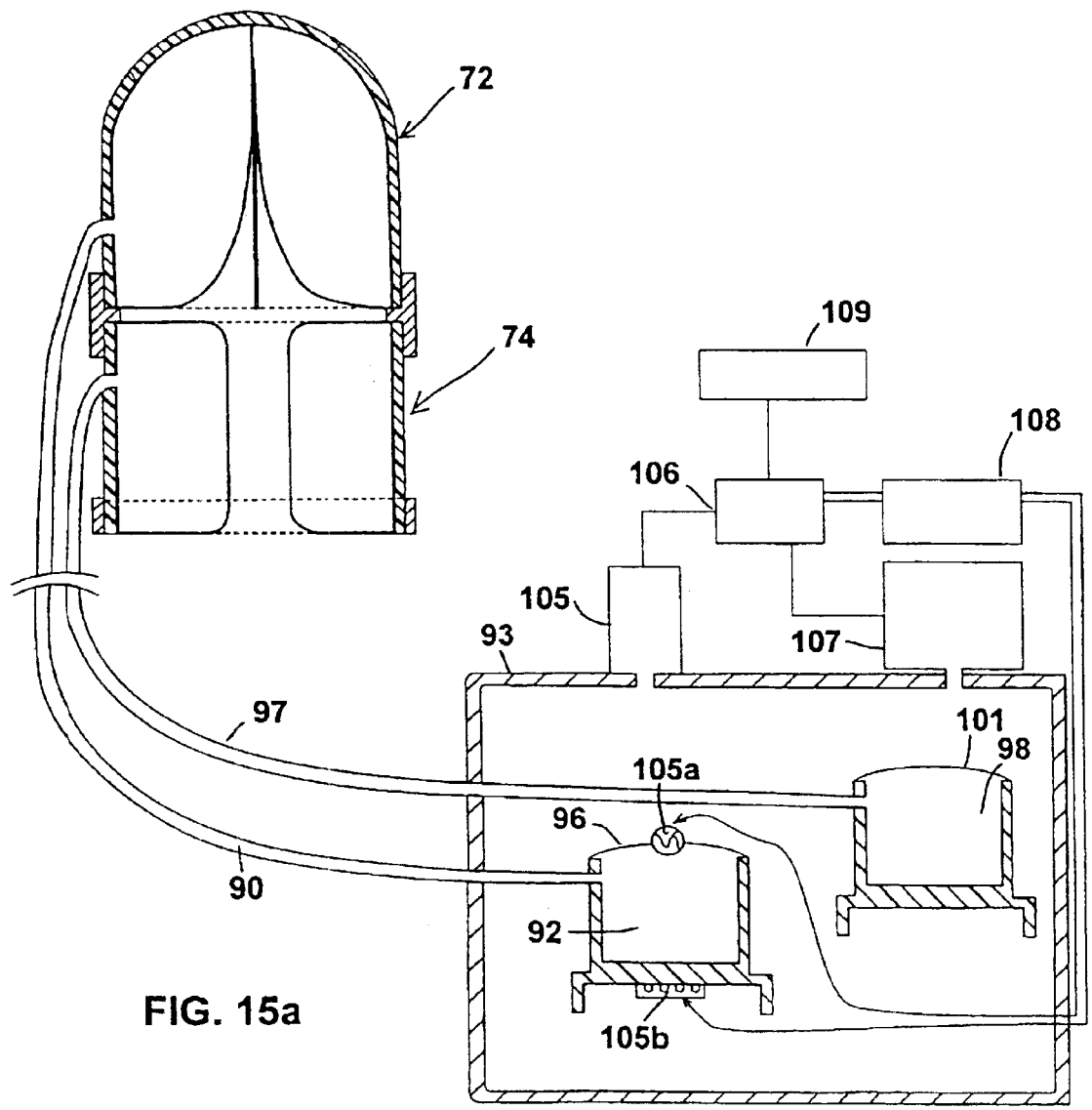
FIG. 15a illustrates an overall apparatus including the probe of FIG. 15.

FIG. 15a illustrates a variation in the construction of the apparatus of FIG. 15, in that the separate housing 93 includes a pressure sensor 150 which senses the pressure within that housing and feeds this information to a CPU 106. The CPU 106 also receives information from the pressure source 107 (e.g. the syringe 102 in FIG. 15) which presets the pressure within housing 93. The output signals from the sensor elements 105a, 105b within housing 93, are also received by CPU 106 after these outputs have been amplified, filtered, and otherwise processed in circuit 108. The CPU 106 processes the foregoing inputs, e.g., as described in the above-cited PCT Application, and produces an output which is displayed in display 109.

In all other respects, the apparatus illustrated in FIG. 15 is constructed and operates in the same manner as described above with respect to FIG. 15, and therefore includes the same reference numerals identifying the corresponding parts.

Figure 16A:
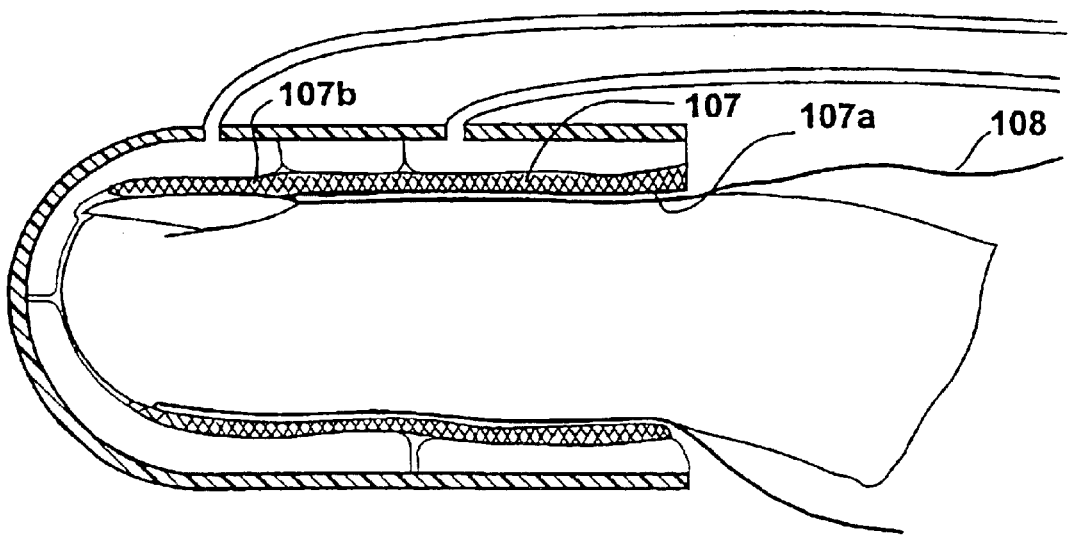

FIGS. 16 and 16a illustrate a finger probe of the same construction as described above, particularly as illustrated in FIGS. 15 and 15a, but including an adhesive layer to be contacted by the patient's finger received within the finger probe. The adhesive layer is provided by a double-sided adhesive strip 107, including an inner adhesive layer 107a and an outer adhesive layer 107b. The inner adhesive layer 107a is covered by a protective layer 108 which is stripped away, after the finger has been inserted within the probe, to enable the inner adhesive layer 107a to contact and firmly adhere to the subject's finger when received within the probe.

In all other respects, the probe illustrated in FIGS. 16 and 16a may be of the same construction as described above, particularly with respect to FIGS. 15 and 15a.

Figure 17:
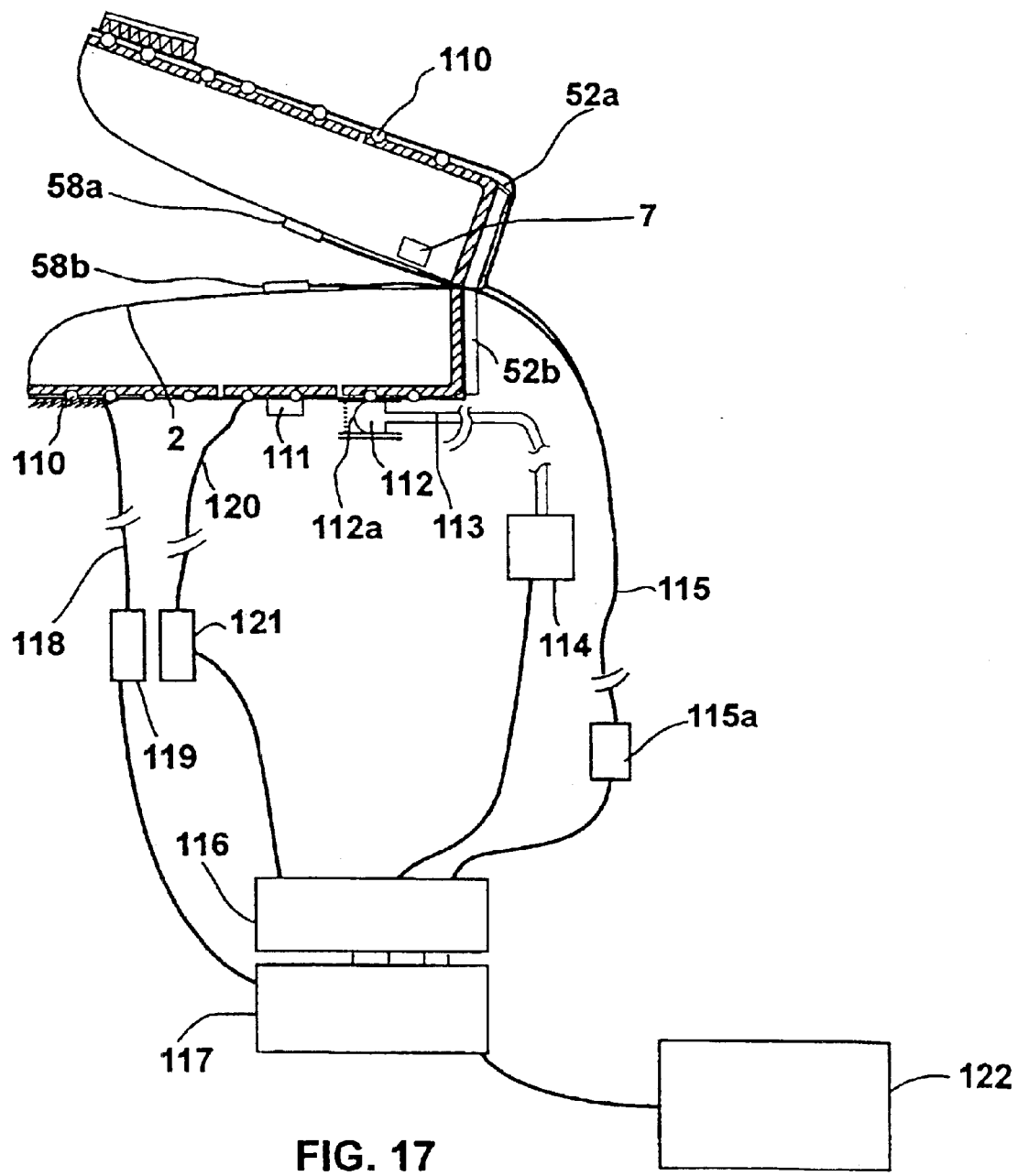
FIG. 17 illustrates an overall apparatus including any of the other described probes.

FIG. 17 illustrates apparatus including the novel finger probe used in apparatus, similar to that described in FIG. 23 of the above-cited PCT Application, for effecting continuous non-invasive blood pressure measurements. For purposes of example, the finger probe illustrated in FIG. 17 is shown as being of the construction described above with respect to FIGS. 11a–11c, although it will be appreciated that it could be of any of the other described constructions.

Thus, the finger probe illustrated in FIG. 17 includes an electrical heater winding 110 applied around the outer surface of the probe housing 52a, 52b for heating the patient's finger within the internal chamber 54a, 54b of the probe to any predetermined temperature, preferably 35–40° C. A thermister 111 or the like controls the electrical heater in order to maintain that temperature so as to dilate the blood vessels in the finger.

The probe illustrated in FIG. 17 further includes a vertical position sensor 112 for sensing the vertical position of the finger probe with respect to a reference point. Sensor 112 may be of the same construction as described in the above-cited PCT Application, including a housing filled with a liquid (preferably water) closed at one end by a flexible membrane 112a and connected at its opposite end via a water filled tube 113 to a pressure transducer 114. Transducer 114 produces an electrical output corresponding to the vertical position of sensor 112, and thereby of the finger probe, with respect to the subject's heart level.

The previously-described sensor elements 58a, 58b of the finger probe are connected via electrical conductors 115 to a circuit 115a for amplifying and processing the output signals, and via an A/D converter 116, to the CPU 117. The electrical heater winding 110 is supplied with power via conductors 118 connected to an electrical power supply 119, also supplying power to the CPU 117. Thermister 111 is connected via conductors 120 to a control circuit 121, which also produces an output to the CPU 117 via the A/D converter 116. CPU 117 produces an output to display 122.

The manner in which the apparatus illustrated in FIG. 17 is calibrated, and then used, for the continuous non-invasive blood pressure measurements is described in the above-cited PCT Application.

FIGS. 18a–18d illustrate a further finger probe device including a self-contained pressurizing source eliminating the need for fluid connections from the probe to an external source of pressurized fluid. In the probe illustrated in FIGS. 18a–18d, however, the pressurizing source for applying the static pressure to the patient's finger is not provided by a fluid chamber within the finger probe as in the previously-described embodiments, but rather is provided by a body of resilient sponge material within the finger probe.

Figure 18A:
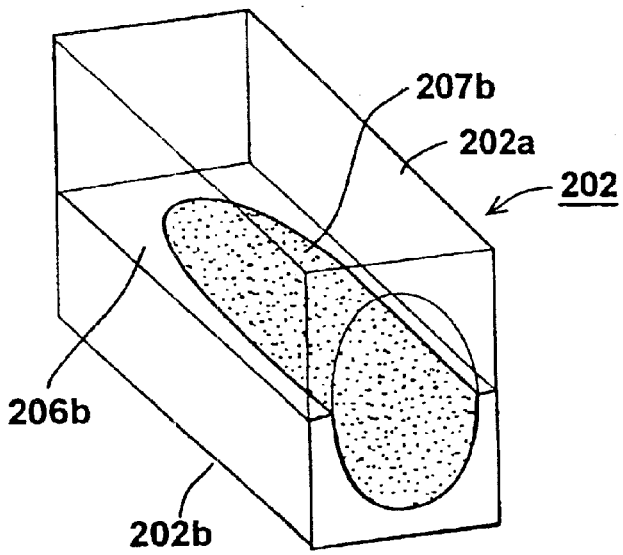
FIGS. 18a–18d diagrammatically illustrate a further probe construction in accordance with the present invention.
Figure 18B:
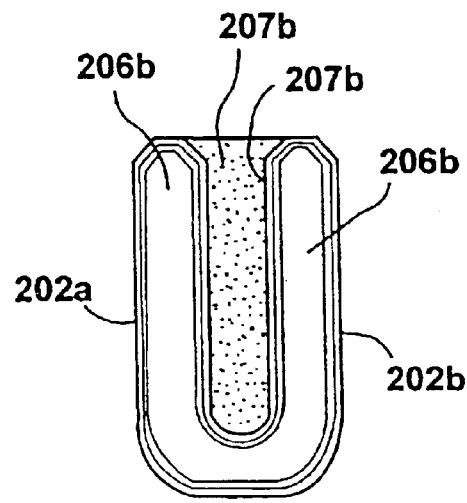
Figure 18C:
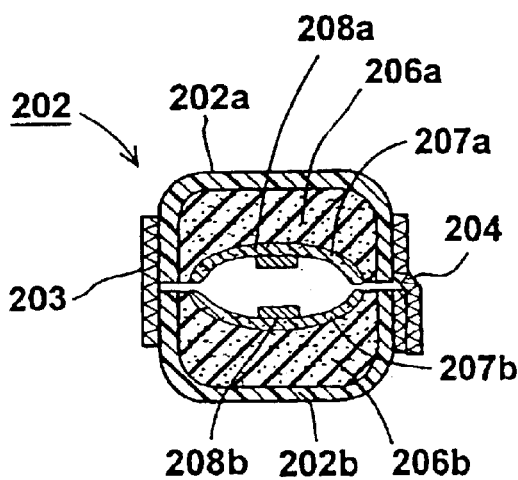
Figure 18D:
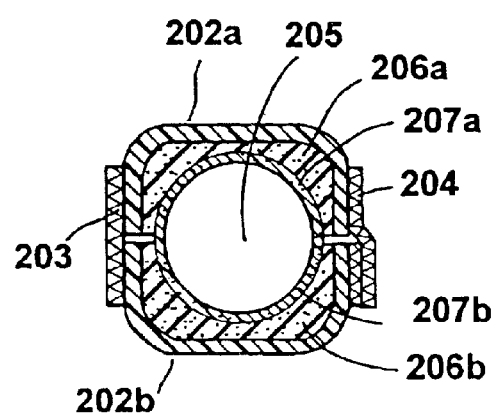

Thus, the finger probe illustrated in FIGS. 18a–18d includes a housing 202 split into two half-sections 202a, 202b, hinged together along one side by a flexible, non-extensible strip 203 and containing "Velcro" (T.M.) strips 204 at the opposite side for tightly clamping the probe to the patient's finger 205 according to the static pressure to be applied. In this case, however, the means for applying the static pressure around the patient's finger is in the form of a body of resilient sponge material 206a, 206b, carried by each half-section of the probe. A layer of a gel material 207a, 207b, covers the inner surface of each of the sponge bodies 206a, 206b so as to be exposed for direct contact with the patient's finger when inserted into the housing and the housing sections are in their closed condition as illustrated in FIGS. 18c and 18d. The sensor elements 208a, 208b, which may be any of the devices described above, are carried on the inner surfaces of each of the sponge bodies 206a, 206b, or their respective gel layers 207a, 207b.

It will be seen that any desired fixed pressure may be applied to the patient's finger within the probe by applying the Velcro strips with the appropriate tightness to the two housing sections around the patient's finger. The gel layers 207a, 207b more securely fix the sponge bodies and their sensor elements to the finger end, and more evenly dissipate the applied force.

While the invention has been described with respect to several preferred embodiments, it will be appreciated that these are set forth merely for purposes of example, and that many other variations may be made. For example, other sensors could be used than the optical and Hall-Effect sensors referred to above, e.g., as described in the above-cited PCT Application. Other fasteners than the "Velcro" or other types described above could be used. Also, the probe may be incorporated in a glove to be worn by the subject as also described in the PCT Application.

Further, the finger probe could be used to house a pulse oximeter for measuring the oxygen saturation of blood. In such an application, conventional pulse-oximeter sensors could be included in the probe housing and would produce a better measurement of the oxygen saturation of the blood ($SaO_2$) because of the stable environment provided by the static pressure field.

It will be appreciated that all the embodiments described with respect to FIGS. 1–17 could be designed to provide the above-described Laplace operation, wherein the distending pressure remains substantially constant substantially constant irrespective of changes in volume. While the probe constructions of FIGS. 18a–18d, including the sponge cushion material would not operate according to the Laplace law, it will be appreciated that a hybrid construction could be provided, wherein the sponge cushion is included to occupy only a part of the chamber containing the sensors and thereby to provide substantially the Laplace operation.

In addition, the invention could be used in applications other than finger probes, e.g., as a supplement to a wound dressing for a body part, as a means for producing venous distention in a body part in prepartion for venapuncture, as a means for supporting, decompressing and/or immobilizing soft tissue injuries like sprains in a wrist or ankle, as a pressure applicatior for edematous regions in a body part, and the like.

Another possible application of the invention is as a disposable sensor, based on a preinflated surface mounted membrane or membranes, capable of being applied to a finger by being wrapped around the finger and having a free end adhesively closed to impart uniform pressure to the enclosed mass of the finger. The membrane(s) may be mounted on an airtight bendable, but non-stretchable material such as plastic sheeting, rubberized cloth, or the like. A tube or tubes would communicate between the finger probe and a sensing console which may be located at the wrist, for example. A unidirectional pressure release valve located at the remote site would ensure that excess pressure is vented from the finger probe upon its initial application.

A further possible application of the invention is in a vertical displacement sensor consisting of a single fluid filled tube connected to an atmospheric pressure referenced pressure transducer at one end, and a compliant tip at the opposite end. The pressure transducer and the compliant tip would be respectively situated at heart level and the measurement site, or vice-versa.

A still further variation would be to provide the probe with the combination of an optical sensor and a volumetric sensor within the same probe. The optical sensing elements need not be located on opposite sides of the finger as described, but could be at other locations. One particularly useful arrangement is that in which optical sensor and light source are respectively placed over the digital arteries, thus being oriented at about 140 degrees with respect to each other.

Many other variations, modifications and applications of the invention will be apparent.

What is claimed is:

1. A device to be applied around a body part of a patient, comprising a probe including:

a housing for application to the body part; and pressurizing means for applying a static pressure field substantially uniformly around the body part, said pressurizing means including:

an inner resilient membrane within said housing and defining therewith an inner chamber to be filled with a fluid for applying said static pressure via said membrane substantially uniformly around a distal end of the body part including a distal tip; and an outer resilient membrane attached to said housing externally thereof and defining therewith an outer chamber communicating with said inner chamber via openings in said housing enlarging an effective volume of said inner chamber such as to cause said inner membrane to apply substantially the same static pressure around the body part despite changes in volume thereof.

2. The device according to claim 1, wherein the body part is a finger.

3. The device according to claim 2, wherein the inner resilient membrane is closed at one end and open at an opposite end to define a compartment for receiving the finger.

* * * * *